US00PP21177P3

(12) United States Plant Patent
Burge

(10) Patent No.: US PP21,177 P3
(45) Date of Patent: Jul. 27, 2010

(54) **VARIETY OF *BEGONIA* PLANT NAMED 'NZCTWO'**

(50) Latin Name: ***Begonia* hybrid**
Varietal Denomination: NZCTWO

(75) Inventor: Garry Kenneth Burge, Palmerston North (NZ)

(73) Assignee: The New Zealand Institute for Plant and Food Research Limited, Palmerston North (NZ)

( * ) Notice: Subject to any disclaimer, the term of this patent is extended or adjusted under 35 U.S.C. 154(b) by 419 days.

(21) Appl. No.: 11/788,075

(22) Filed: Apr. 19, 2007

(65) Prior Publication Data

US 2008/0263736 P1 Oct. 23, 2008

(51) Int. Cl.
*A01H 5/00* (2006.01)

(52) U.S. Cl. ..... Plt./343

(58) Field of Classification Search ..... Plt./343
See application file for complete search history.

*Primary Examiner*—Annette H Para
(74) *Attorney, Agent, or Firm*—Fulwider Patton LLP

(57) ABSTRACT

A new and distinct cultivar of *Begonia* plant named 'NZCTWO' characterized by a medium bushy growth habit with burgundy and browned green foliage and a reddish pink flower.

1 Drawing Sheet

BACKGROUND OF THE NEW PLANT

The present invention relates to a new and distinct cultivar of *Begonia* plant, botanically known as *Begonia* hybrid, and further known by the varietal name 'Nzctwo'. The new variety may also be referred to commercially in the future as 'Bellfire.' The new variety was derived from a population of seeds collected from other begonias grown in Palmerston North, New Zealand. The unnamed seed parent was identified as a *Begonia micranthera* and *Begonia boliviensis* hybrid plant that had been back-crossed to *Begonia boliviensis* (seed parent), where the pollen parent is a *Begonia boliviensis* clone. Following selection of the seedling, the cultivar was developed by cross pollination in April 2002, which preceded selection in February 2004. The plant was asexually reproduced via cuttings in Palmerston, North, New Zealand. The selected cultivar should only be propagated by asexual means, i.e. by cuttings. The new plants were grown in a bark and pumice medium in six inch plastic bags. Continued observation of future generations have confirmed that the distinguishing features of this new cultivar remain stable and are retained through successive asexual reproduction via cuttings. The measurements and observations of the plants were taken outdoors from plants grown in soil under sunny conditions on Jan. 12, 2007.

The comparator 'NZCONE' has a reddis orange flower color and forest green upper side with light green lower side leaf color. This variety 'Nzctwo' has reddish pink flower color and browned green upper side with burgundy lower side leaf color.

SUMMARY OF THE INVENTION

Plants of the cultivar 'NZCTWO' have not been observed under all possible environmental and cultural conditions. The phenotype of the new cultivar may vary somewhat with variations in environment such as temperature, light intensity, length of day, irrigation amount and frequency, and/or fertilizer rate without, however, any variance in genotype.

The following traits have been repeatedly observed and are determined to be among the unique characteristics of 'NZCTWO'. These characteristics distinguish 'NZCTWO' as a new and distinct cultivar from its closest comparator *Begonia boliviensis* 'NZCONE':

1. Reddish pink flowers; and
2. Leaves with browned green colored upper sides and burgundy colored lower sides.

Compared to other plants of the *Begonia* genus, the new *Begonia* has distinctive flowers of reddish pink color.

BRIEF DESCRIPTION OF THE DRAWINGS

The invention is depicted in the accompanying colored photograph in which:

FIG. 1 shows a potted plant illustrating the characteristic foliage and flowers.

The photograph depicts the overall appearance of the new *Begonia*, showing the colors as true as it is reasonably possible to obtain in colored reproductions of this type. Colors in the photograph may differ slightly from the color values cited in the Detailed Botanical Description which more accurately describe the actual colors of the new *Begonia*.

DETAILED BOTANICAL DESCRIPTION OF THE NEW PLANT

The following detailed description sets forth characteristics of the new cultivar. The data which defines each characteristic was collected from reproductions of the plant. The plant histories of *Begonia* 'NZCTWO' were taken outdoors in soil under sunny conditions on Jan. 12, 2007.

In the following table of plant characteristics, color references are made to The Royal Horticultural Society of London Colour Chart, 1995 Edition. The age of the plant described is approximately one year old with measurements taken from mature leaves.

THE PLANT

Classification:

*Botanical.*—*Begonia* hybrid.

*Varietal Name.*—'NZCTWO'.

*Parentage.*—cross pollination of *Begonia boliviensis* and *Begonia micranthera*.

*Asexual propagation.*—cross pollination cutting.

Form:

*Plant Growth Rate.*—Moderate.

*Growth Habit.*—Upright.

*Plant Density.*—Bushy.

*Growth Type.*—Shrub.

*Mean Plant Height.*—0.8 meters.

*Mean Plant Width.*—0.8 meters.

*Stem.*—

*Mean stem diameter.*—10.18 mm.

Leaves:

*Leaf Color.*—upside: browned green (slightly darker than RHS 147A 1995) with lighter green veins; lowerside: burgundy (RHS 187B, 1995).

*Mean Leaf width (mm).*—36.06 mm.

*Mean Leaf Length (mm).*—72.18 mm (excluding petiole).

*Leaf Characteristics.*—Apex—Deeply serrated Margin—Undulated Texture—Coarse, textured Shape—Lancolate Base—Closed Flower Characterics.—Pedicel Prickles: none Bud shape—Flattened ovate Flower size—18–25 mm (as viewed from above) Flower profile upper—flat Flower profile lower—convex Inflorescence—single male at apex, duel female laterals Sepal—Two below female inflorescence Number of petals—Four Petal Size—small to medium Petal Width—mean: 11.5 mm Petal Length—mean: 29 mm Petal Arrangement—overlapping Pedicel Length—mean: 26.75 Pedicel Color—burgundy (RHS 185A, 1995) Number of Flowers—many Color midzone outside—39B (RHS ed. 1995) Color midzone inside—39B (RHS ed. 1995) Color Margin inside—Reddish pink Color Basal spot—None Filament color—yellow Anther—yellow Style color—light yellow Seed Vessel Characteristics Size—10–12 mm Color—brownish green Type of asexual propagation to establish stability-cutting Growth rate—Flowers in first seasons growth, dormant in winter. Flower buds—reddish pink, flattened ovate; male flower length longer than width; petals elongate on opening, petals open together, inner petals reflex first before opening into a bell shaped flower prior to abscission. Reproductive—monoecious, larger male flower at apex of flowering bract, duel female flowers as laterals with a winged seed capsule: stamens, column shaped color yellow, approximately 30; pollen color: yellow, pistals color: yellow, style color: light yellow, style shape: twisted; ovaries contain six seed pods.

Duration- continuous tuberous *begonia* Disease Resistance—very good disease resistance

GENERAL CHARACTERISTICS

'NZCTWO' is distinguished from other cultivars of *Begonia* genus by its foliage of browned green on the upper side and burgundy on the lower side, and its inflorescence including reddish pink flowers. 'NZCTWO' is an upright bushy shrub with lancolate leaves having a serrated edge and closed base.

What is claimed is:

1. A new and distinct *Begonia* hybrid plant named 'NZCTWO' substantially as illustrated and described.

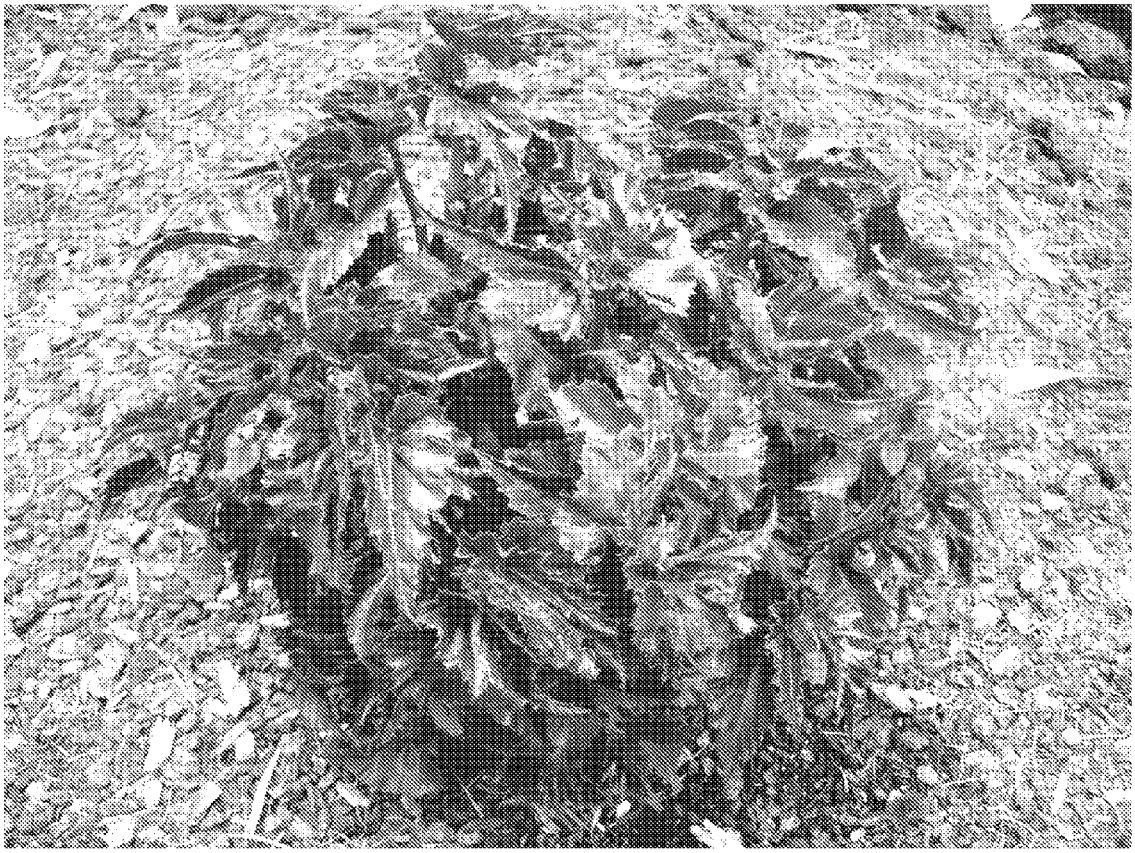

* * * * *